US009563817B2

(12) United States Patent
Holt

(10) Patent No.: US 9,563,817 B2
(45) Date of Patent: Feb. 7, 2017

(54) APPARATUS AND METHOD FOR RECONSTRUCTING AN IMAGE USING HIGH-ENERGY-BASED DATA

(71) Applicant: Varian Medical Systems, Inc., Palo Alto, CA (US)

(72) Inventor: Kevin M. Holt, Chicago, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 83 days.

(21) Appl. No.: 14/532,741

(22) Filed: Nov. 4, 2014

(65) Prior Publication Data
US 2015/0125061 A1 May 7, 2015

Related U.S. Application Data
(60) Provisional application No. 61/899,672, filed on Nov. 4, 2013.

(51) Int. Cl.
*G06K 9/00* (2006.01)
*G06K 9/60* (2006.01)
(Continued)

(52) U.S. Cl.
CPC ............... *G06K 9/60* (2013.01); *G06T 5/001* (2013.01); *G06T 5/50* (2013.01); *A61B 6/482* (2013.01);
(Continued)

(58) Field of Classification Search
CPC ......... A61B 6/482; A61B 6/5211; G06K 9/60; G06T 2207/10116; G06T 5/001; G06T 5/50
See application file for complete search history.

(56) References Cited

U.S. PATENT DOCUMENTS 6,005,916 A * 12/1999 Johnson ................. A61B 5/05
378/87
8,184,769 B2 * 5/2012 Fox ...................... A61B 6/4035
378/53
(Continued)

OTHER PUBLICATIONS

Blomgren, Peter et al.; "Color TV: Total Variation Methods for Restoration of Vector-Valued Images," IEEE Transactions on Image Processing, vol. 7, No. 3; 1998; 6 pages.
(Continued)

*Primary Examiner* — Gandhi Thirugnanam
(74) *Attorney, Agent, or Firm* — Fitch, Even, Tabin & Flannery LLP

(57) ABSTRACT

An apparatus reconstructs an image using high energy-based data regarding a scene provides access to first image-capture data regarding the scene that is formed using a first image-capture modality and to second image-capture data that is formed using a second (different) image-capture modality. A control circuit executes an iterative image reconstruction process that establishes a first and a second image-representation channel, a fidelity error measure that measures inconsistency of the image as compared to first image-capture data and second image-capture data, and a prior-penalty term that scores the image based on a priori likelihood or desirability using, at least in part, for each of a plurality of pixels, a non-separable matrix-penalty of a Jacobian-matrix of the image at that pixel, such as nuclear norm. The control circuit further utilizes, in combination with the foregoing, an iterative process to generate a reconstructed image that at least approximately minimizes a combination of the fidelity error measure and the prior-penalty term.

21 Claims, 5 Drawing Sheets

(51) Int. Cl.
*G06T 5/00* (2006.01)
*G06T 5/50* (2006.01)
*A61B 6/00* (2006.01)

(52) U.S. Cl.
CPC ..... *A61B 6/5211* (2013.01); *G06T 2207/10116* (2013.01)

(56) References Cited

U.S. PATENT DOCUMENTS

| 8,422,826 | B2* | 4/2013 | Holt | G06T 5/50 345/634 |
|---|---|---|---|---|
| 2006/0084859 | A1* | 4/2006 | Johnson | A61B 5/0507 600/407 |
| 2006/0287596 | A1* | 12/2006 | Johnson | A61B 5/4312 600/437 |
| 2008/0071164 | A1* | 3/2008 | Pogue | A61B 5/0091 600/411 |
| 2011/0311121 | A1* | 12/2011 | Zhang | G06T 7/0034 382/131 |
| 2012/0133779 | A1* | 5/2012 | Ma | G06K 9/6249 348/175 |
| 2013/0101156 | A1* | 4/2013 | Holt | G01N 23/06 382/103 |
| 2014/0029829 | A1* | 1/2014 | Jiang | A61B 8/13 382/131 |
| 2014/0090491 | A1* | 4/2014 | Holt | G01J 3/28 73/865.9 |
| 2015/0125061 | A1* | 5/2015 | Holt | G06T 5/001 382/132 |
| 2015/0363947 | A1* | 12/2015 | Rigie | G06T 11/005 382/131 |
| 2016/0171727 | A1* | 6/2016 | Bouchard | G06T 11/008 382/131 |

OTHER PUBLICATIONS

Bresson, Xavier et al.; "Fast Dual Minimization of the Vectorial Total Variation Norm and Applications to Color Image Processing," American Institute of Mathematical Sciences; Inverse Problems and Imaging, vol. 2, No. 4; 2008; pp. 455-484.

Goldluecke, Bastian et al.; "An Approach to Vectorial Total Variation Based on Geometric Measure Theory," IEEE Computer Society Conference on Computer Vision and Pattern Recognition; Jun. 2010; 7 pages.

Goldluecke, Bastian et al.; "The Natural Vectorial Total Variation Which Arises from Geometric Measure Theory," SIAM Journal on Imaging Sciences; vol. 5, No. 2; Jan. 2012; 27 pages.

* cited by examiner

|          |          |          |
|----------|----------|----------|
|          | NEIGHBOR |          |
| NEIGHBOR | PIXEL    | NEIGHBOR |
|          | NEIGHBOR |          |

*FIG. 3B*

| PIXEL OF INTEREST | NEIGHBOR |
|-------------------|----------|
| NEIGHBOR          |          |

*FIG. 3A*

|   | N | N | N |   |
|---|---|---|---|---|
| N | N | N | N | N |
| N | N | P | N | N |
| N | N | N | N | N |
|   | N | N | N |   |

*FIG. 3D*

| NEIGHBOR | NEIGHBOR | NEIGHBOR |
|---|---|---|
| NEIGHBOR | PIXEL | NEIGHBOR |
| NEIGHBOR | NEIGHBOR | NEIGHBOR |

*FIG. 3C*

APPARATUS AND METHOD FOR RECONSTRUCTING AN IMAGE USING HIGH-ENERGY-BASED DATA

RELATED APPLICATION(S)

This application claims the benefit of U.S. Provisional application No. 61/899,672, filed Nov. 4, 2013, which is incorporated by reference in its entirety herein.

TECHNICAL FIELD

These teachings relate generally to reconstructing images using high energy-based data as regards a particular scene, and in particular to approaches that rely upon statistical likelihoods.

BACKGROUND

The use of statistical reconstruction to facilitate iterative reconstruction of an image through a series of consecutive estimations and/or guesses is a known area of prior art endeavor. Such an iterative statistical reconstruction process typically works by characterizing candidate reconstructed image data with respect to an overall likelihood of accuracy (and/or some other metric of choice) to thereby identify a best selection.

Transitions in an image (for example, from one object to another such as, in an x-ray image, from bone to water, or from less-dense bone to more-dense bone) often represent a considerable challenge in these regards. Generally speaking, an iterative statistical reconstruction process works favorably when configured to eschew unrealistic transitions. Furthermore, measurement noise can lead to false transitions appearing in the data, and in general a good statistical reconstruction process should account for the measurement noise, in effect removing or reducing the false transitions. That said, transitions, even abrupt transitions, can and do occur in the real world, and in an ideal imaging system those real transitions should be preserved. Accordingly, accommodating real transitions (especially abrupt transitions) but downgrading a candidate reconstructed image having one or more false transitions is both a goal and a challenge.

Statistical reconstruction also generally requires the use of optimization algorithms. Many approaches to optimization in these regards are known. In many cases the practical applicability of a given approach in a given application setting is limited by the computational intensity dictated by that setting and approach. While many approaches are ultimately capable of providing an acceptable result, from a practical standpoint in a real-life application setting many approaches either take too much time to converge, require too much in the way of computational resources to physically implement for a reasonable cost, are unstable or unpredictable, and/or are inflexible with the types of statistical models that they can accommodate.

BRIEF DESCRIPTION OF THE DRAWINGS

The above needs are at least partially met through provision of the apparatus and method for reconstructing an image using high energy-based data described in the following detailed description, particularly when studied in conjunction with the drawings, wherein:

FIGS. 3A-F comprise block diagram representations of various pixel neighborhoods.

Figure 1:
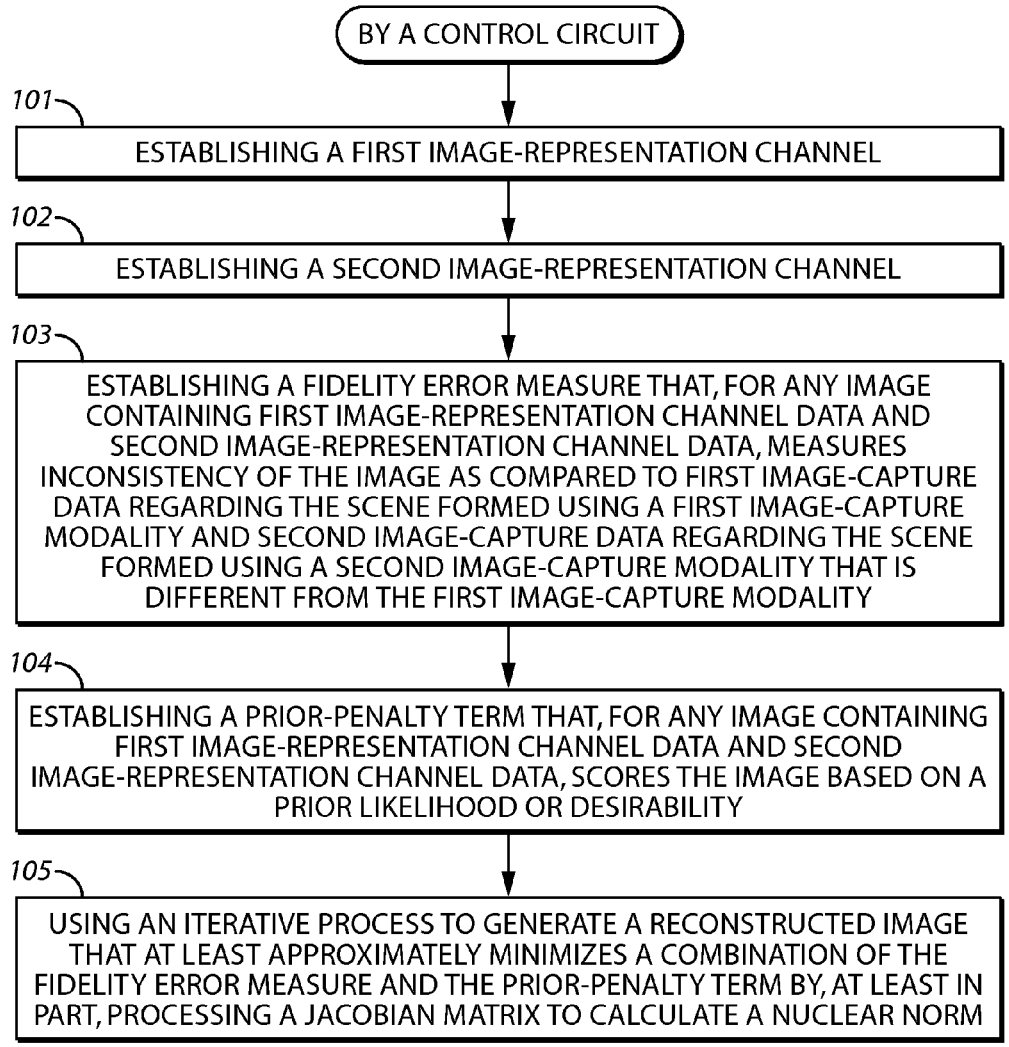
FIG. 1 comprises a flow diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

There are many existing approaches to statistical reconstruction methods for X-ray imaging, and a key difference between them is how they handle transitions. In particular, many existing approaches penalize abrupt transitions and prefer smooth transitions, and such methods tend to destroy true abrupt transitions in the images. Better methods are able to penalize a lot of the false transitions yet still preserve some real transitions, especially large abrupt transitions. However, most of these methods are designed for use with a single imaging spectrum.

Alternatively, many modern X-ray imaging systems use multiple spectra to be able to discriminate different types of materials beyond what they are capable of with just a single spectrum. In such multi-spectral X-ray systems, when considering abrupt transitions, I have determined that it is important to consider not only transitions in attenuation, but also transitions in material type. More specifically, I have determined that it can be important to consider transitions in the higher dimensional material signature in the multi-spectral measurements (as opposed to scalar attenuation values, density values, or Hounsfield-unit values), and furthermore that it can be important to consider transitions in multiple material channels and in multiple spatial directions, and to consider these transitions together in a coupled way that is not separable by channel or spatial direction. Existing approaches are in general inadequate in this regard.

Generally speaking, pursuant to these various embodiments an apparatus for reconstructing an image using high energy-based data regarding a scene (such as a portion of a patient being examined or a cargo container being inspected) includes a data interface and a control circuit operably coupled thereto. The data interface provides access to, at least in part, first image-capture data regarding the scene, which first image-capture data is formed using a first image-capture modality. The data interface also provides access to second image-capture data regarding the scene, which second image-capture data is formed using a second image-capture modality that is different from the first image-capture modality.

The control circuit executes an iterative image reconstruction process. This activity includes establishing a first and a second image-representation channel and establishing a fidelity error measure that, for any image containing first image-representation channel data and second image-representation channel data, measures inconsistency of the image as compared to the first image-capture data and the second image-capture data. The control circuit also establishes a prior-penalty term that, for any image containing first image-representation channel data and second image-representation channel data, scores the image based on a priori likelihood or desirability using, at least in part, for each of a plurality of pixels, a non-separable matrix-penalty of a Jacobian matrix at that pixel. The control circuit further utilizes, in combination with the foregoing, an iterative process to generate a reconstructed image that at least approximately minimizes a combination of the fidelity error measure and the prior-penalty term. By one approach, the non-separable matrix-penalty is a function of the singular values of the Jacobian matrix. More specifically, the non-separable matrix-penalty can be the nuclear norm of the Jacobian matrix, which is the sum of the singular values of the Jacobian matrix.

These teachings are highly flexible in practice and will accommodate a variety of approaches as regards the foregoing. By one approach, for example, the first image-capture modality can comprise using a first level of x-ray energy while the second image-capture modality comprises using a second level of x-ray energy that is substantially different from the first level of x-ray energy.

By one approach, the control circuit effects the foregoing by using the first image-representation channel and the second image-representation channel to evaluate individual pixels in the image-representation data with respect to statistical likelihood. This can comprise, for example, assessing a gradient for at least some of the individual pixels as compared to their corresponding neighboring pixels. More particularly, the control circuit can calculate a function of both the gradient as corresponds to the first image-representation channel for a given pixel and the gradient as corresponds to the second image-representation channel for the same given pixel by, at least in part, forming a corresponding Jacobian matrix that the control circuit then employs to calculate a function of the singular values of the Jacobian matrix, such as the aforementioned nuclear norm. By another approach, the control circuit can in calculate a function of the singular values of the Jacobian matrix, but can combine some steps in the calculations so that the Jacobian matrix or the singular values are not explicitly formed along the way.

So configured, these teachings employ the above described disparate inputs regarding a given scene when reconstructing an image as corresponds to that scene. By one approach, for example, the control circuit utilizes that disparate input to effectively evaluate candidate reconstructions by viewing at least some components of those reconstructions as a function of their material constitution. As a very simple illustrative example in these regards, the control circuit can evaluate the accuracy and/or desirability of reconstructed patient x-ray-based images upon treating the components of those reconstructed images as constituting either bone or not-bone.

These teachings can also readily handle an arbitrary number of image representation channels, for which prior art can be inadequate. For example, a method that quantifies the ratio between two channels can be difficult to extend to a third channel. In contrast, vector-penalties of singular values of a matrix can be straightforward to apply to singular value vectors of any dimension, and thus can be used for Jacobians of any dimension and for any number of material channels.

Prior art approaches tend to use separable penalties and/or a small number of material channels (usually both), so that any given calculation employs relatively low-dimensional matrices or vectors (typically at most 2×1 vectors), and higher-dimensionality matrices might be viewed as prohibitive. However, these teachings will also allow higher-dimensionality matrices to be accurately and quickly calculated and utilized as compared to prior art approaches that would employ the same enabling hardware. Generally speaking, these teachings will provide resultant reconstructed images that are either equal to results attained through common prior art practices or, perhaps more typically, better without necessarily or unduly prolonging the calculation of those results.

These and other benefits may become clearer upon making a thorough review and study of the following detailed description. Referring now to the drawings, and in particular to FIG. 1, an illustrative process 100 that is compatible with many of these teachings will now be presented.

Figure 2:
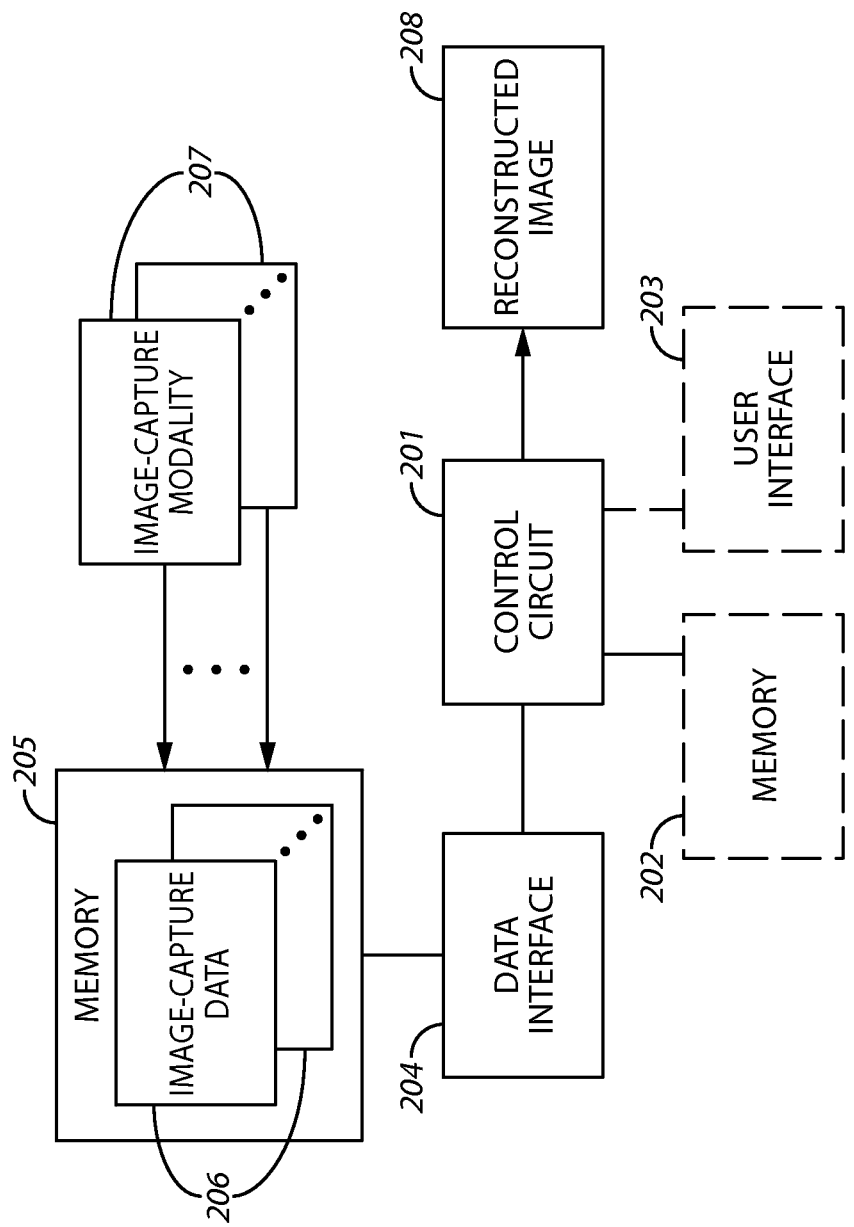
FIG. 2 comprises a block diagram as configured in accordance with various embodiments of these teachings.

For the sake of an illustrative example this description will presume that a control circuit of choice carries out the described process 100. FIG. 2 provides an illustrative example in these regards. In this example the enabling apparatus 200 includes a control circuit 201 that operably couples to a memory 202 and a user interface 203. Such a control circuit 201 can comprise a fixed-purpose hard-wired platform (such as an application specific integrated circuit (ASIC)) or can comprise a partially or wholly programmable platform (such as a field-programmable gate array or a fully-programmable microcontroller or microprocessor). These architectural options are well known and understood in the art and require no further description here. This control circuit 201 is configured (for example, by using corresponding programming as will be well understood by those skilled in the art) to carry out one or more of the steps, actions, and/or functions described herein.

The memory 202 may be integral to the control circuit 201 or can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

This memory 202 can serve, for example, to non-transitorily store the computer instructions that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The user interface 203 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

The data interface 204 provides a link or conduit by which the control circuit 201 receives useful data. This data interface 204 may simply be an on-board communicative conduit between the control circuit 201 and a corresponding memory 205 (which memory 205 may or may not be part of the aforementioned memory 202 as desired). By another approach this data interface 204 may comprise, for example, a network interface that communicatively couples the control circuit 201 to one or more data sources via, for example, a local area network and/or an extranet such as the Internet.

In this illustrative example the data interface 204 operably couples to a memory 205 that includes image-capture data 206 as regards a particular scene of interest. More particularly, the memory 205 includes a plurality of image-capture data 206 for each such scene. For purposes of simplicity and clarity, this description will presume that there are first and second image-capture data 206. Although these instances of image-capture data 206 correspond to a same scene, these instances of image-capture data 206 were each formed using a different image-capture modality. In particular, in this example, the first image-capture data regarding the scene was formed using a first image capture modality 207 while the second image capture data regarding the scene was formed using a second image-capture modality 207 that is different from the first image-capture modality 207.

These teachings are highly flexible in these regards and will accommodate considerable variety with respect to these differing image-capture modalities. As one simple example, the first image-capture modality may comprise using 120 kV x-ray spectra to capture corresponding first image-capture data as regards the scene and the second image-capture modality comprising using 140 kV x-ray spectra to capture corresponding second image-capture data as regards the scene.

As another example, the first image-capture modality may comprise detecting incoming X-rays with a first region or layer of detector material, and the second image-capture modality comprising detecting incoming the same X-ray beam with a second region or layer of detector material on the same detector. As yet another example, the first and second image-capture modalities may comprise different outputs from a pulse-height discriminating detector. Again, numerous possibilities in these regards can be readily accommodated by these teachings. These teachings can also be used with more than two modalities. For example, in the above example with 120 kV and 140 kV x-ray spectra, a third modality may comprise 95 kV x-rays, or another 120 kV beam with different filtration. Additionally, the above techniques may be combined, such as by using multiple X-ray source energies in conjunction with energy-sensitive detectors. If desired, these teachings can readily accommodate a number of modalities much larger than two.

As described below in more detail, the control circuit 201 is configured to employ an iterative process to generate a reconstructed image 208 that at least approximately minimizes a combination of a fidelity error measure and a prior-penalty term by, at least in part, processing a Jacobian matrix to calculate a matrix-penalty function of the Jacobian matrix, such as nuclear norm.

Referring again to FIG. 1, at block 101 the control circuit establishes a first image-representation channel and, at block two, a second image-representation channel. These teachings are flexible in these regards. By one approach, for example, the first image-representation channel relates to a first basis material and the second image-representation channel relates to a second basis material. A basis material can be a real or imaginary material, and corresponds to some material component, and any real material can be decomposed, at least approximately, into a sum of basis materials.

By one approach, these bases may be actual materials. For example, one may choose water and bone as the two bases, and every material is reconstructed into an equivalent amount of water and bone. As other materials may be present, it is possible that some other material may be decomposed into, for example, over 100% water in conjunction with a negative amount of bone.

By another approach, these bases may relate to physical interactions. For example, the first basis may correspond to an amount of photo-electric interaction, and the second basis may correspond to an amount of Compton interaction. In either of those two approaches, the system may explicitly form basis functions that describe some physical interaction characteristics. For example, for X-ray imaging with water and bone bases, the energy-dependent X-ray attenuation of some material $\mu(E)$ is modeled as $\mu(E)=\alpha_{water}\mu_{water}(E)+\alpha_{bone}\mu_{bone}(E)$, where the $\mu_{water}$ and $\mu_{bone}$ curves are known ahead of time, and $\alpha_{water}$ and $\alpha_{bone}$ are the two image-representation channels that are calculated by the reconstruction algorithm. Similarly, for photo-electric and Compton bases, each material is decomposed into $\mu(E)=\alpha_{water}\mu_{water}(E)+\alpha_{bone}\mu_{bone}(E)$ where $\alpha_{water}$ and $\alpha_{bone}$ are the two image-representation channels.

By another approach, the basis materials can be formed by constructing mathematically appealing basis functions, without a real physical interpretation for each basis material. For example, one can design a set of basis functions to be an approximate mathematical basis for the set of commonly occurring $\mu(E)$ functions (for example, by using a singular value decomposition), so that most any physically plausible $\mu(E)$ can be reasonably well approximated using those basis materials.

By a fourth approach, the material bases may relate to imaging spectrum. For example, the first basis may correspond directly to the first imaging modality, and the second basis may correspond directly to the second imaging modality. This may be done explicitly, similar to the above examples, by using different pre-computed $\mu$ for each basis (though $\mu_1$ and $\mu_2$ might now be scalar-valued rather than curves).

Or alternatively, the bases may be only implicitly used rather than explicitly defined. This approach can also be used when the physical interpretation of the channels is unknown by the image processing system. For example, this approach can be used to build a black-box reconstructor that accepts multi-spectral data but requires no knowledge of the actual characteristics of the spectra used to produce that data. (As an extreme example, even if an imaging system has already performed multi-modality fusion and rendered the data as a conventional red, green, and blue (RGB) image, the present teachings can still be used to reduce noise in that image by processing the red, green, and blue channels, even though their physical interpretations are lost.)

At block 103 the control circuit 201 establishes a fidelity error measure that, for any image containing first image-representation channel data and second image-representation channel data, measures inconsistency of the image as compared to first image-capture data regarding the scene informed using the aforementioned first image-capture modality and second image-capture data regarding the scene formed using the aforementioned second image-capture modality that is different from the first image-capture modality. By one approach, this difference between modalities can be one of degree (where, for example, both modalities employ x-ray spectra but differ with respect to the energy level), a difference of kind, or one of both kind and degree as desired.

At block 104 the control circuit 201 establishes a prior-penalty term that, for any image containing first image-representation channel data and second image-representation channel data, scores the image based on a priori likelihood or desirability using, at least in part, for each of a plurality of pixels, a non-separable matrix-penalty of a Jacobian matrix at that pixel. (As used herein, this reference to "likelihood" shall be understood to refer to a statistical likelihood and this reference to "desirability" shall be understood to refer to one or more metrics as correlate to one or more objective or subjective measures of aesthetic and/or interpretive rendering criterion (such as diagnostic information of interest or information regarding diagnostic capability).

At block 105 the control circuit 201 then uses an iterative process of choice to generate a reconstructed image that at least approximately minimizes a combination of the aforementioned fidelity error measure and the aforementioned prior-penalty term by, at least in part, processing a Jacobian matrix to calculate a non-separable matrix penalty. So configured, the nuclear norm facilitates assessing an abrupt transition in an image, at least in part, by assessing whether a corresponding edge for that transition as considered with respect to the first image-representation channel registers with the corresponding edge for that transition as considered with respect to the second image-representation channel. When true, the likelihood increases that the abrupt transition is, in fact, a valid feature of the image.

By one approach, and in accordance with the foregoing, the control circuit 201 generates the reconstructed image 208 by, at least in part, using the first image-representation channel and the second image-representation channel to evaluate individual pixels in the image-representation data with respect to statistical likelihood. This evaluation of individual pixels can comprise, at least in part, assessing a gradient for at least some of the individual pixels as compared to their corresponding neighboring pixels. (In mathematics, the gradient is a generalization of the usual concept of derivative of a function in one dimension to a function in several dimensions. If $f(x_1, \ldots, x_n)$ is a differentiable, scalar-valued function of standard Cartesian coordinates in Euclidean space, its gradient is the vector whose components are the n partial derivatives of $f$. It is thus a vector-valued function. Furthermore, if the function $f$ is a vector-valued function so that at point x, $f(x_1, \ldots, x_n)=(v_1, \ldots, v_m)$, then for each of the m components, there is a separate gradient, which itself has n components. In that case the derivative of $f$ at any x can be arranged as an m×n matrix (or an n×m matrix) which is often referred to as the Jacobian matrix. We refer to n as different directions, and m as different channels.)

For example, the control circuit 201 can calculate a function of both the gradient as corresponds to the first image-representation channel for a given pixel and the gradient as corresponds to the second image-representation channel for a same given pixel, at least in part, by forming a corresponding Jacobian matrix that the control circuit 201 then employs to calculate the aforementioned non-separable matrix-penalty. (The Jacobian is the generalization of the gradient for vector-valued functions of several variables and differentiable maps between Euclidean spaces. In vector calculus, a Jacobian matrix is the matrix of all first-order partial derivatives of a vector-valued function.) In prior art, typically the gradient of an image is calculated by a finite difference operator.

Figure 3F:
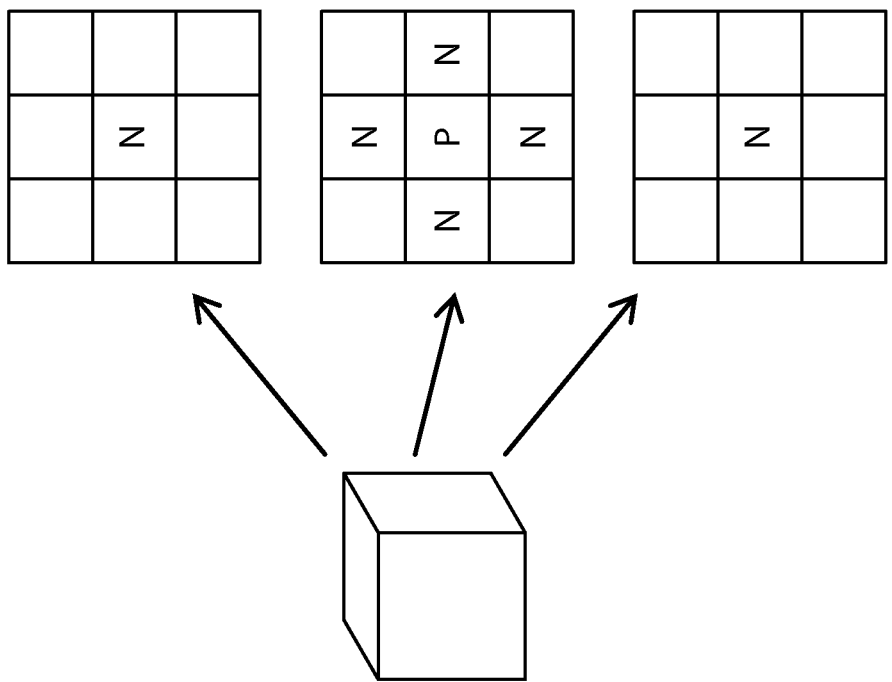
Figure 3E:
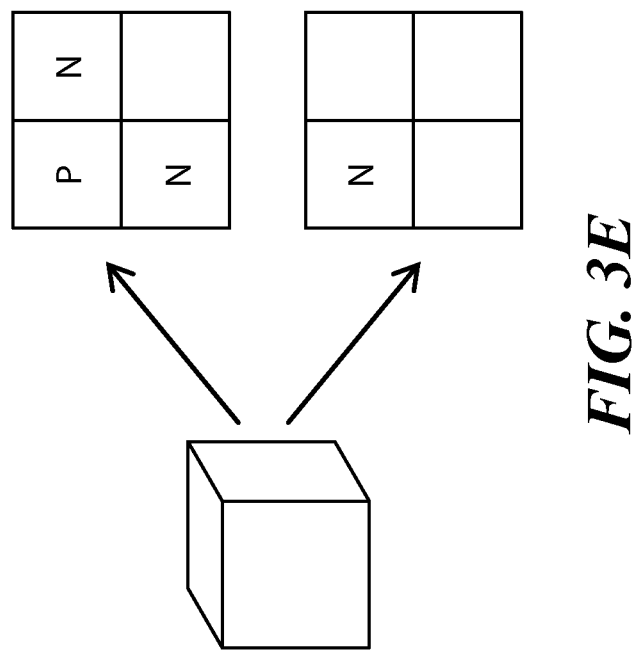

This is illustrated for 2D in FIG. 3A. Each pixel has two relevant neighbors, and n=2. Alternatively, the applicant has determined that in many cases, extended Jacobians can give better image quality, where an extended Jacobian uses something larger than the basic finite-difference operator. FIG. 3B depicts, for example, a cross-shaped neighborhood, which uses four neighbors, so n=4. FIG. 3C depicts a 3×3 box-shaped neighborhood, for which n=3. FIG. 3D depicts a 5×5 circle-shaped neighborhood, for which n=20. Similarly, for three dimensional images, FIG. 3E depicts the standard finite-difference operator, with n=3, and FIG. 3F depicts a 3D cross-shaped neighborhood, with n=6.

There are many other reasonable neighborhoods to use for extended Jacobians. Furthermore, these teachings will show how to accommodate large Jacobian matrices (for example 20×2 or 20×3 Jacobian matrices) with reasonable computational load. Note that we use the term "Jacobian matrix" to include both conventional Jacobians as well as extended Jacobians.

In general, we define a "matrix-penalty" to mean a function that inputs a matrix and outputs a single scalar score for that matrix (where typically "good" matrices get a small-valued score and larger values indicate a worse matrix). When applying a matrix penalty to a Jacobian matrix, prior art approaches typically construct matrix-penalties by analyzing separate channels or directions (or both) in relative isolation. When a matrix-penalty of a Jacobian matrix can be calculated by separately calculating a penalty for each channel in the Jacobian matrix and then summing the results, we call that a channel-separable matrix-penalty. When a matrix-penalty of a Jacobian matrix can be calculated by separately calculating a penalty for each direction in the Jacobian matrix, then summing the results, we call that a direction-separable matrix-penalty. When a matrix-penalty of a Jacobian matrix is neither channel-separable nor direction-separable, we call that a non-separable penalty.

The teachings described here can be used with penalties that are channel-separable, direction-separable, both channel- and direction-separable, or that are non-separable. While direction-separable techniques have been used in prior art, the applicant has determined that non-separable techniques are able to better link the gradients for different directions and different channels. In particular, a particularly effective class of non-separable matrix-penalty is to penalize a function of the singular values of the Jacobian matrix. In particular, the nuclear norm, which is the sum of the singular values of a matrix, can be quite effective.

As noted above, by one approach the image-representation channels can comprise corresponding material bases. As one useful example in these regards, the establishment of a first image-representation channel can comprise establishing a first material basis and the aforementioned establishment of a second image-representation channel can comprise establishing a second corresponding material basis. In such a case the first image-representation channel describes image data as relates to the first material basis and the second image-representation channel describes image data as relates to the second material basis. So configured, these teachings essentially operate to encourage or otherwise favor candidate reconstructed images comprised of pixels that tend to have neighboring pixels made of the same material. For example, pixels representing bone material in a radiographic image are favored that themselves have neighboring pixels made of bone material as well.

Put simply, the present teachings leverage the fact that activity on the first material basis should usually appear similar to activity on the second material basis (in particular, for most pixels in an image, a gradient for a pixel should change in the same way for each material basis) and anomalies in those regards help to identify transitions that are less likely to be accurate. In particular, whereas channel-separable Jacobian matrix penalties do not encourage each material basis to change in tandem, and direction-separable Jacobian matrix penalties do not encourage the material change to be the same in each direction, non-separable matrix penalties, and in particular penalties based on singular values of the Jacobian matrix, encourage change to be proportional for all materials in all directions, which helps to mitigate false transitions in material. Furthermore, nuclear norm mitigates false transitions in material while also allowing occasional abrupt transitions when the data supports them, since it essentially assigns the same penalty to transitions regardless of whether they are smooth or abrupt.

In many cases it will be beneficial for the aforementioned iterative process to comprise an iterative statistical reconstruction process. Such an iterative statistical image reconstruction process can comprise, if desired, a computed tomography reconstruction process or a radiography-image reconstruction process. Other possibilities can be accommodated as well if desired.

To illustrate by way of example, and without intending any particular limitations by way of the specificity of the following examples, some further details in these same regards are now presented.

In particular, this example provides details regarding how to perform reconstruction of a material-descriptor image as described in terms of a general projection operator. By one approach, the projection operator is a tomographic projection operator that sums along paths in the reconstructed image, in effect mapping densities to ray-sums (or some function thereof). Such tomographic projection operators are known in the art, and any tomographic forward/backward projector pair can be used to implement these teachings. In this approach, these teachings are applicable in a computed tomography setting and more specifically in a multi-spectral computed tomography setting. By specifying the appropriate projection operator, this approach can accommodate or enable a number of desirable features in CT reconstruction, including novel geometries, sparse detectors, tomosynthesis, few views, or unusual trajectories as well as alternate modalities and/or multi-modality fusion.

By another approach, the projection operator can map ray-sums to ray-sums, for example by performing a simple resampling, by selecting out sparse data (i.e. masking out missing data), by applying a blur function (to model detector blur), or by simply doing nothing (which in practice can be implemented by simply omitting the projection operator). This approach can serve in a radiography (or even a fluoroscopy) medical-services application as well as an industrial or security application setting. By specifying the appropriate projection operator, this approach can accommodate or enable a number of desirable features in radiography, including denoising, deblurring, super-resolution, restoring missing data, fluoroscopy enhancement, material-discrimination, dual-energy (or multi-energy) digital subtraction angiography, virtual bone subtraction, and multi-spectral fusion.

In this example, expected transmission for a material descriptor $\alpha$ is $$\overline{T}_k(\alpha) = \sum_i \phi_{i,k} e^{-\sum_j \mu_{i,j}\alpha} = \sum_i \phi_{i,k} e^{-\langle-\mu,\alpha\rangle} \quad (1)$$

where k is spectrum index, i is like energy bin, $\phi$ is like spectrum, $\mu$ is like attenuation curve, j is like material index, and $\alpha$ describes the material. (We say "like" because in many cases these can be represented in a more compact mathematical form than the physical entity that inspires them.) Poisson log likelihood for measured data T and expected ("truth") signal $\overline{T}$ are (to within an additive constant)

$$\log Pr[T|\overline{T}] = \omega(\overline{T} - T \log \overline{T}) \quad (2)$$

where $\omega = SNR_o^2$ (similar to weighted least-squares fitting) and/or $SNR_o$ is signal-to-noise ratio through air (i.e. when T=1). Then we can write multi-spectral log likelihood as a function of $\alpha$ as follows:

$$\ell(\alpha) = -\log Pr[T|\overline{T}(\alpha)] = \sum_k \omega_k (\overline{T}_k(\alpha) - T_k \log \overline{T}_k(\alpha)). \quad (3)$$

If $\alpha$ is an image formed of pixels, then the image likelihood is $$L(\alpha) = \sum_x \ell(\alpha(x)) \quad (4)$$

where x is a pixel.

We can thus pose statistically reconstructed multi-spectral radiography or multi-spectral computed tomography by the problem $$X^* = \underset{X}{\operatorname{argmin}} \omega_p L(PX) + \omega_v V(X) + \omega_c \overline{C}(X) \quad (5)$$

where V is some regularization term, $\overline{C}$ is a constraint or feasibility measure (generally the indicator function of a constraint such as non-negativity), and P is a projection operator. For computed tomography, X corresponds to a density map (with separate densities for each material basis), and P is typically a forward fan-beam or cone-beam transform (and $P^t$ is back projection). For radiography (including dual-energy medical imaging, or material-discrimination (MD) security imaging, X represents a map of total projected material, and P is typically either the identity P=I or a simple resampling operator or a simple linear blur. The $\omega$ values are relative weights for each of the three terms.

When V is a Jacobian-based regularizer, one can rewrite Equation 5 as $$\underset{X_p,X_v,X_c,X_r}{\operatorname{minimize}} \omega_p L(X_p) + \omega_v R(X_v) + \omega_c C(X_c) \quad (6)$$

subject to $X_p = PX_r$, $X_v = HX_r$, $X_c = QX_r$ where:

subscripts r, p, v, and c stand for reconstruction, projection, variation, and constraints;

X, is the reconstructed image, which is the same as X from Equation 5;

$X_p$ is the projected data;

$X_v$ is the gradient of the reconstructed image;

$X_c$ is the constrained image;

H is a gradient (or extended gradient) operator applied to each channel (so $HX_r$ is an image Jacobian);

$$R(X_v) = \sum_x \phi(X_v(x))$$

for some matrix penalty $\phi$ so that V(X)=R(HX), where nuclear norm $\phi=\|\cdot\|_*$ is a good choice;

Q is a helper transform (or matrix) to help C have convenient structure (in many cases this may just be the identity Q=I, where in practice Q is essentially omitted from the implementation);

C is chosen so that $\overline{C}(X)=C(QX)$, and C is an indicator for whether every pixel is a member of some set S, so $C(Y) = \Sigma_x \iota_S(Y(x))$ where $\iota_S(y)=0$ when $y \in S$ and $\infty$ otherwise.

Equation 6, in turn, can be written as a special case of the generalized split problem $$\underset{x_0,\ldots,x_N}{\text{minimize}} \sum_{i=0}^{N} f_i(x_i) \quad (7)$$

$$\text{subject to } A_i x_i + B_i x_0 + c = 0 \, \forall \, i \in 1{:}N,$$

where in our case $$x_0=X_r, \, x_1=X_p, \, x_2=X_v, \, x_3=X_c, \, f_0=0, \, f_1=\omega_p l, \, f_2=\omega_v R,$$
$$f_3=\omega_c C, \, A_1=I, \, A_2=I, \, A_3=I, \, B_1=-P, \, B_2=-H,$$
$$B_3=-Q. \quad (8)$$

There are several primal dual algorithms available in the literature that are appropriate for solving problems such as this, including Arrow-Hurwicz, Bermudez-Moreno/Chambolle algorithm, FISTA, Chambolle & Pock's method, split Bregman methods, or alternating direction method of multipliers (ADMM). We will consider here the use of ADMM and in particular the use of ADMM for regularized material reconstruction.

1. Initialize
(a) Choose some values for $\rho_p$, $\rho_v$, $\rho_c$.
(b) Set $X_r$ to be some initial guess. (Either a good guess using existing algorithms that are fast but less accurate, or a very simple guess (that might be terrible) like all zeros).
(c) Set $\lambda_p$, $\lambda_v$, and $\lambda_c$ to be images of all zeros.
(d) Choose $\zeta=1$ for unaccelerated ADMM, or $1<\zeta<2$ for accelerated ADMM.

2. Set up proximal points for separate problems $$Y_p = PX_r - \frac{1}{\rho_p}\lambda_p \quad (9)$$

$$Y_v = HX_r - \frac{1}{\rho_v}\lambda_v \quad (10)$$

$$Y_c = QX_r - \frac{1}{\rho_c}\lambda_c \quad (11)$$

3. Do these steps independently for each pixel, where "prox" is Moreau proximal mapping, and $\Pi_S$ is projection onto the set S:

$$X_p \approx \text{prox}_l^{\rho_p/\omega_p}(Y_p) \quad (12)$$

$$X_v = \text{prox}_\phi^{\rho_v/\omega_v}(Y_c) \quad (13)$$

$$X_c = \Pi_S(Y_c) \quad (14)$$

4. Set up proximal points for the fusion problem $$Z_p = -\zeta X_p + (1-\zeta)PX_r - \frac{1}{\rho_p}\lambda_p \quad (15)$$

$$Z_v = -\zeta X_v + (1-\zeta)HX_r - \frac{1}{\rho_v}\lambda_v \quad (16)$$

$$Z_c = -\zeta X_c + (1-\zeta)QX_r - \frac{1}{\rho_p}\lambda_c \quad (17)$$

5. Then perform these global/fusion steps $$\hat{X}_r \approx \text{argmin}\left(\frac{\rho_p}{2}\|PX + Z_p\|^2 + \frac{\rho_v}{2}\|HX + Z_v\|^2 + \frac{\rho_c}{2}\|QX + Z_c\|^2\right) \quad (18)$$

$$\lambda_p = \lambda_p + \rho_p(\zeta X_p - (\zeta-1)PX_r - P\hat{X}_r) \quad (19)$$

$$\lambda_v = \lambda_v + \rho_v(\zeta X_v - (\zeta-1)HX_r - H\hat{X}_r) \quad (20)$$

$$\lambda_c = \lambda_c + \rho_c(\zeta X_c - (\zeta-1)QX_r - Q\hat{X}_r) \quad (21)$$

$$X_r = \hat{X}_r \quad (22)$$

Repeat steps 2 through 5.

To solve Equation 12 above, a simple solution is to apply a few iterations of the conjugate gradient (CG) method, so for each pixel $$X_p = \text{minimize}_X^{CG} \omega_p \ell(X) + \frac{\rho_p}{2}\|X - Y_p\|^2. \quad (23)$$

Another option is to perform a damped Newton iteration, by replacing Equation 12 with $$X_p \approx \text{minimize}_X \omega_p \ell(X) + \frac{\rho_p}{2}\|X - Y_p\|^2 + \frac{\gamma}{2}\|X - X_p^{prev}\|^2 \quad (24)$$

whose solution is $$g^n = \nabla\left(\omega_p \ell(X_p^n) + \frac{\rho_p}{2}\|X_p^n - Y_p\|^2\right) = \omega_p \nabla \ell(X_p^n) + \rho_p(X_p^n - Y_p) \quad (25)$$

$$H^n = \text{Hessian}\left(\omega_p \ell(X) + \frac{\rho_p}{2}\|X\_Y_p\|^2\right) = \omega_p \nabla^2 \ell(X) + \rho_p I \quad (26)$$

$$X_p^{n+1} = X_p^n - (H^n + \gamma^n I)^{-1}(g_n + \gamma^n(X - X_p^{prev})) \quad (27)$$

This is nicely parallelizable since one can have a different $\gamma$ for each pixel. If ($H^n+\gamma^n I$) becomes noninvertible, one can increase $\gamma$ (say, by a factor of 10) for that pixel. Otherwise, one can decrease $\gamma$ by a small amount every iteration (say, multiply by 0.9). One skilled in these arts can readily employ code to calculate H for multi-spectral polychromatic Poisson log-likelihood that performs the above calculations. The parallel nature of the computations make them well suited for implementation on a standard graphics processing unit (GPU), for example by using the compute unified device architecture (CUDA) platform from nVidia corporation. Such an approach can easily accommodate tens or hundreds of energy bins, as well as material descriptors of relatively arbitrary dimension.

By one approach the code can be written (say, in CUDA) with a hard-coded material dimension. By another approach, the code can be written to use a user-provided material dimension, so that the same code is applicable to a wider range of applications and settings. In this latter approach, it can be advantageous to write low-level code (say, CUDA device code) that specifies the material descriptor dimension as a template parameter (using standard C++ templates), but then higher level code (say, CPU code) that dynamically chooses which pre-compiled version of the lower-level code to call. This approach gives the best of both worlds, as the low-level code is actually compiled separately and optimized separately for each material-dimension size, so for small material dimensions the calculations can take place mostly in registers or local cache, but yet the high-level code still offers flexibility to an end user.

In practice, this approach can be used to make good use of CUDA register space for material dimensions of 10 or less, and possibly even higher. Thus for typical applications with a modest number of modalities, most of the math is done in registers or local cache and it is therefore very fast as compared to comparable (or even less serviceable) prior art approaches.

An alternate strategy would be to use surrogate functions to solve Equation 12. In particular, parabolic or paraboloid surrogates (as known in the art) can be very efficient.

To solve Equation 13, one can apply proximal mapping. A useful class of matrix-penalties are Schatten norms, which can be calculated by first calculating the singular values of a matrix, then taking the conventional vector norm of the vector of singular values. In light of the present teachings there are three particularly interesting Schatten norms to use as $\phi$. The Schatten 1-norm is also commonly called nuclear norm, and is a good choice for $\phi$, in which case we refer to the function R as Total Nuclear Variation (TNV). The Schatten 2-norm is also commonly called Frobenius norm, and when it is used for $\phi$ we call the function R Total Frobenius Variation (TFV). The Schatten co-norm is also commonly called spectral norm, operator 2-norm, or induced 2-norm, and when it is used for $\phi$ we call the function R Total Spectral Variation (TSV). For 1-dimensional Jacobians, the solution to (13) for any Schatten norm is $$X_v = \begin{cases} \frac{Y_v}{\|Y_v\|}\left(\|Y_v\| - \frac{\rho_v}{\omega_v}\right) & \text{if } \|Y_v\| > \frac{\rho_v}{\omega_v}, \\ 0 & \text{if } \|Y_v\| \le \frac{\rho_v}{\omega_v}. \end{cases} \quad (28)$$

For higher dimensional matrices, for TFV regularization, the prox map is essentially the same as Equation 28, just using a Frobenius norm. For TNV regularization (which may be preferred for many application settings), the update can be performed as follows. Say that Y is M×N, where one of the two dimensions (M or N) corresponds to the dimension of the material descriptors (or equivalently, the number of image-representation channels, or equivalently, the number of material bases), and the other dimension corresponds to spatial direction (i.e., 2 for 2D imaging and a standard gradient, 3 for 3D imaging with a standard gradient, or larger numbers when using extended gradients). Note that the implementation below applies regardless of which dimension is which.

In any case, we begin by calculating matrices U, S, V where U and V are orthogonal matrices containing the singular vectors of Y, and S is the singular values of Y, so if we express S as a diagonal matrix then Y=U S V$^t$. The first step is to calculate the minimal symmetric matrix. If N≤M, this is A=(Y$^t$Y). If M≤N, this is A=(Y Y$^t$). If M=N, use either form. Note that A is now a square matrix of size min(M,N).

The next step is to find the eigenvalues of A. This is well-known in the art, and for small dimensions has especially efficient solutions based on the characteristic polynomial. When A is 1×1, there is a single eigenvalue which is simply equal to A. When A is 2×2, the characteristic polynomial is a quadratic equation, and thus the two eigenvalues can be efficiently found through the quadratic formula, which is a simple closed-form expression that is known in the art. Similarly, when A is 3×3, the three eigenvalues can be found by solving a cubic equation, and when A is 4×4, the four eigenvalues can be found by solving a quartic equation. While less common than the quadratic formula, cubic equations and quartic equations also have efficient closed-form solutions known in the art. There are also more general methods known in the art that apply to square matrices of any size.

The next step is to take the square roots of the eigenvectors—this yields the singular values of Y. The next step is then to find the eigenvectors. First we find the smaller set of eigenvectors by using the Cayley-Hamilton theorem, and next we find the larger set of eigenvectors by factoring the singular-value decomposition. That is, if we chose A=(Y$^t$ Y) then we solve for V using the Cayley-Hamilton theorem, and then calculate U=Y V S$^{-1}$ Alternatively, if we chose A=(Y Y$^t$) then we solve for U using the Cayley-Hamilton theorem, and then calculate V=Y U S$^{-1}$.

Once the singular-value decomposition is available, we apply a shrinkage operator to the singular values, so $$\hat{S} = \begin{cases} \frac{S}{\|S\|}\left(\|S\| - \frac{\rho_v}{\omega_v}\right) & \text{if } \|S\| > \frac{\rho_v}{\omega_v}, \\ 0 & \text{if } \|S\| \le \frac{\rho_v}{\omega_v}. \end{cases}$$

Lastly, the solution to Equation 13 is found by $X_v = U \hat{S} V^t$. While these steps may seem complicated, in practice, they can be calculated very efficiently.

In particular, consider when min(M,N)=2, which involves the quadratic solution. This corresponds to the case of 2D imaging (i.e. conventional radiography or 2D CT) with a conventional gradient and with material descriptors of any dimension (i.e. of dimension 2 or larger). It also corresponds to the case of 3D (or higher) CT reconstruction of 2D material descriptors (which are typical for dual energy), whether using conventional or extended gradients. It also corresponds to the case of 2D imaging with an extended gradient and 2D material descriptors. In the example where M=2 and then the steps to solve (13) for some pixel are:

$$z = Y_v \quad (29)$$

-continued $$G \stackrel{def}{=} zz^t \qquad (30)$$

$$\xi \stackrel{def}{=} \sqrt{(g_{11} - g_{22})^2 + 4g_{12}^2}, \qquad (31)$$

$$S(1) = \sqrt{\frac{1}{2}(g_{11} + g_{22} + \xi)}, \qquad (32)$$

$$S(2) = \sqrt{\frac{1}{2}(g_{11} + g_{22} - \xi)}, \qquad (33)$$

$$u_{11} = \begin{cases} \sqrt{\frac{g_{11} - g_{22} + \xi}{2\xi}} & \text{if } \xi \neq 0, \\ 1 & \text{if } \xi = 0, \end{cases} \quad u_{21} = \begin{cases} \frac{g_{12}}{u_{11}\xi} & \text{if } \xi \neq 0, \\ 0 & \text{if } \xi = 0, \end{cases} \qquad (34)$$

$$u_{12} = u_{21}, \qquad u_{22} = -u_{11},$$

$$V = z^t U S^{-1} \qquad (35)$$

$$\hat{S} = \begin{cases} \frac{S}{\|S\|}\left(\|S\| - \frac{\rho_v}{\omega_v}\right) & \text{if } \|S\| > \frac{\rho_v}{\omega_v}, \\ 0 & \text{if } \|S\| \leq \frac{\rho_v}{\omega_v}, \end{cases} \qquad (36)$$

$$X_v = U\hat{S}V^t. \qquad (37)$$

The foregoing can be done quite efficiently. Furthermore, it may be performed independently for each pixel, with almost no "if" statements, so one skilled in the art can implement Equation 13 in a highly parallel fashion which is well-suited to implementation on commodity GPU cards. While the cubic and quartic solutions (for min(M,N)=3 or 4) are considerably more complicated than the above, they also are very well-suited to efficient parallel implementations in CUDA. Since CUDA's texture units additionally offer native support for 2D and 3D images where each pixel is up to a 4D vector, the entire system can be especially optimized for imaging with up to 4-dimensional material descriptors.

Additionally note that the bulk of the processing work is generally for the singular-value factoring, whose dimension is limited by min(M,N). Thus, if the material descriptor dimension is 4 or less, then the number of spatial-directions can be much larger (for example, 20 or more) with an additional computational cost that is relatively small. Conveniently, this makes large extended Jacobians reasonable to use in practice.

Note that the above approach can also be extended to any Schatten norm by using the appropriate shrinkage operator. It can also be extended to any conventional vector-penalty applied to the singular values of the Jacobian by replacing the above shrinkage operator with the appropriate proximal mapping for the desired vector-penalty.

To solve Equation 14 one can perform a projection onto the set S. Often this has very simple solutions. For example, if we want to enforce a non-negativity constraint so that $X_c(i) \geq 0$ for all i, then S is the set of vectors whose components are all non-negative, or equivalently $S = \{x : x(i) \geq 0 \forall i\}$. In this case, Equation 14 simply becomes $$X_c(i) = \begin{cases} Y_c(i), & \text{if } Y_c(i) \geq 0 \\ 0 & \text{if } Y_c(i) \leq 0 \end{cases} \forall i. \qquad (38)$$

More generally one might desire the constraint $BX_c > 0$ for some matrix B. In this case, to implement Equation 14 there are known algorithms for projecting a vector onto a set of hyperplanes. Alternatively, one can move B into the matrix Q so that C becomes a simple non-negativity constraint, which saves computations, but consumes more memory (if BX is larger than X) and will make Equation 18 more complicated.

Note that if constraints are not used, or if they can be incorporated into the log-likelihood term, then one can simply set $\omega_c = \rho_c = 0$ and omit steps (11), (14), (17), and (21) and drop the last term from Equation 18.

To solve Equation 18 the approach depends greatly on the projection operator, i.e. on whether we are performing radiography or CT. The naïve solution is $$\hat{X}_r = -(\rho_p P^t P + \rho_v H^t H + \rho_c Q^t Q)^{-1}(\rho_p P^t Z_p + \rho_v H^t Z_v + \rho_c Q^t Z_c). \qquad (39)$$

The matrix inversion, however, can benefit from some additional consideration. There are several approaches to solving Equation 18 or 39 at least approximately.

One approach is to solve Equation 39 exactly by using a discrete cosine transformation (DCT). This approach is suitable each of the operators P, H, and Q are equivalent to convolution operations. In this case, Equation 39 can be solved exactly using a DCT, which yields symmetric boundary conditions (Equation 39 can also be solved using a fast Fourier transform, but that gives cyclic boundary conditions, which are typically less desirable). To solve Equation 39, the following can be repeated independently for each material dimension.

The DCT version assumes that P is a convolution with a blur kernel b (which may be different for each material dimension), H is a set of convolutions with kernels $h_1, \ldots h_n$ (one for each spatial direction), and that Q=I. The update (for each material dimension) is $$\hat{X}_r = D^{-1}\left\{F^{-1}D\left\{\rho_p Z_p \boxtimes \tilde{b} + \rho_c Z_c + \rho_v \sum_j Z_v \boxtimes \tilde{h}_{j=1}^n\right\}\right\} \qquad (40)$$

where $\tilde{b}$ and $\tilde{h}$ are symmetric reflections of b and h, and D is the type-II DCT, and $$F = D_I\left\{\rho_p \text{orth}(b * \tilde{b}) + \rho_c \delta + \rho_v \sum_{j=1}^n \text{orth}(h_j * \tilde{h}_j)\right\} \qquad (41)$$

where $D_I$ is the type-I DCT, orth means take one orthant of the signal, and $\delta$ is a kronecker delta function. Note that $F^{-1}$ can be precomputed once during the initialization phase. If the $\rho$ values change during the course of the optimization, the separate components of F can still be precomputed during initialization. Since this approach solves Equation 39 exactly, it is the optimal approach in terms of minimizing the total number of iterations of Equations 9-22. This approach can be particularly effective for radiography, where the projection operator P is commonly either the identity mapping or it only applies a simple linear blur (to model the detector point spread function).

A second approach is Bregman operator splitting (BOS) as known in the art, where one replaces the matrix inversion in Equation 39 with a simple uniform scaling.

$$\hat{X}_r = -\frac{1}{\alpha}(\rho_p P^t Z_p + \rho_v H^t Z_v + \rho_c Q^t Z_c) \qquad (42)$$

where α is chosen to be at least as big as the operator norm of the matrix inside the inversion in Equation 39. If P=I and Q=I then $\alpha = \rho_p + \rho_c + 4n\rho_r$ is a good choice.

Under the same assumptions as Equation 40, i.e. when P is a blur with kernel b, H is a set of convolutions with kernels $h_1, \ldots h_n$, and Q=I, then Equation 42 becomes $$\hat{X}_r = -\frac{1}{\alpha}\left(\rho_p Z_p \boxtimes \tilde{b} + \rho_c Z_c + \rho_v \sum_{j=1}^n Z_v \boxtimes \tilde{h}_j\right). \quad (43)$$

Conveniently however, Equation 42 does not carry the same restrictions (or assumptions) as Equation 40. That is, Equation 42 can be used for arbitrary P, H, or Z operators. In particular, Equation 42 can be used for tomography where P is a forward-projection operator. Equation 42 can also be applied to radiography or other reconstruction tasks with other types of P or Q mappings, such as if P also includes a resampling operator or missing data, or if Q couples different spectral channels. Note that if H is convolutions with a set of h kernels, then Equation 42 becomes $$\hat{X}_r = -\frac{1}{\alpha}\left(\rho_p P^t Z_p + \rho_c Q^t Z_c + \rho_v \sum_{j=1}^n Z_v * \tilde{h}_j\right). \quad (44)$$

In general, this approach is useful for CT reconstruction; for radiography with complicated P, Q, or H operators; or for radiography with simple operators but where a DCT is too expensive to implement (in terms of effort, computational time, or required computational resources).

Another approach, specifically for CT reconstruction, is to use analytic CT reconstruction theory. It is known in the art that if P is a forward-projection operator (so $P^t$ is a back-projection operator), then ($P^t$ P) is at least approximately equivalent (or exactly equivalent, in the continuous limit) to convolution with the function 1/|f|, where f is frequency. Using that, Equation 39 can be solved by $$\hat{X}_r = -F^{-1}\left\{\beta F\left\{\rho_p P^t Z_p + \rho_c Z_c + \rho_v \sum_j Z_v * \tilde{h}_j\right\}\right\}$$

where

F is the Fourier transform (typically a fast Fourier transform (FFT));

$$\beta = \frac{|f|}{\rho_r + \rho_c|f| + \rho_v|f|\sum_j |F\{h_j\}|^2};$$

and in practice, β can be pre-computed during initialization. To prevent artifacts, the terms can also be adjust with some custom filter or apodization window, as are known in the art.

This approach requires good sampling and is not suitable for sparse measurement data, and it also risks noise amplification and truncation issues, but when those downsides are manageable, this approach can potentially reduce the number of iterations required for CT relative to some other alternatives.

Yet another approach is to use conventional continuous optimization techniques on Equation 18. For example, define $$q(X) \stackrel{def}{=} \frac{\rho_p}{2}\|PX + Z_p\|^2 + \frac{\rho_v}{2}\|HX + Z_v\|^2 + \frac{\rho_c}{2}\|QX + Z_c\|^2. \quad (45)$$

then $$\hat{X}_r \approx \arg\min_X q(X) \quad (46)$$

which can be performed with gradient descent (or conjugate gradients) by noting that $$\nabla q = \rho_p P^t(PX + Z_p) + \rho_v H^t(HX + Z_v) + \rho_c Q^t(QX + Z_c) \quad (47)$$

or a Newton or quasi-Newton method by also noting that $$\nabla^2 q = \rho_p P^t P + \rho_v H^t H + \rho_c Q^t Q. \quad (48)$$

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept. Some useful examples in these regards may be found in one or more of the following patent applications/patents, the contents of which are hereby fully incorporated herein in their entirety by this reference: U.S. patent application Ser. No. 13/277,833 filed Oct. 20, 2011; U.S. patent application Ser. No. 13/630,269 filed Sep. 28, 2012; U.S. Pat. No. 8,422,826 which issued Mar. 27, 2013; U.S. Pat. No. 8,184,769 which issued May 22, 2011; and U.S. Pat. No. 8,508,545 which issued Aug. 13, 2013.

As a more specific example in these regards these teachings will accommodate further employing third image-capture data regarding the scene that is formed using a third image-capture modality that is different from the first image-capture modality and the second image-capture modality, wherein the aforementioned fidelity error measure further measures the inconsistency of the image as compared to the third image-capture data. As a similar related example, these teachings will also accommodate establishing a third image-representation channel, and then measuring the inconsistency of the image by also measuring the inconsistency of the image as compares to third image-representation channel data and scoring the image based on a priori likelihood or desirability by scoring an image that further comprises third image-representation channel data.

What is claimed is:

1. An apparatus for reconstructing an image using high energy-based data regarding a scene, the apparatus comprising:
   a data interface configured to provide access to:
      first image-capture data regarding the scene formed using a first image-capture modality;
      second image-capture data regarding the scene formed using a second image-capture modality that is different from the first image-capture modality;
   a control circuit operably coupled to the data interface and configured to execute an iterative image reconstruction process by, at least in part:
      establishing a first image-representation channel;
      establishing a second image-representation channel;
      establishing a fidelity error measure that, for any image containing first image-representation channel data and second image-representation channel data, measures inconsistency of the image as compared to the first image-capture data and the second image-capture data;

establishing a prior-penalty term that, for any image containing first image-representation channel data and second image-representation channel data, scores the image based on a priori likelihood or desirability using, at least in part, for each of a plurality of pixels for that image that contains the first image-representation channel data and the second image-representation channel data, a non-separable matrix-penalty of a Jacobian-matrix of the image at that pixel;

using an iterative process to generate a reconstructed image for which the reconstructed image at least approximately minimizes a combination of the fidelity error measure and the prior-penalty term.

2. The apparatus of claim 1 wherein the first image-capture modality comprises using a first level of x-ray energy and the second image-capture modality comprises using a second level of x-ray energy that is substantially different from the first level of x-ray energy.

3. The apparatus of claim 1 wherein the control circuit is configured to generate the reconstructed image by, at least in part, using the first image-representation channel and the second image-representation channel to evaluate individual pixels in the image-representation data with respect to statistical likelihood.

4. The apparatus of claim 1 wherein the control circuit is configured to evaluate the individual pixels by, at least in part, assessing a gradient for at least some of the individual pixels as compared to their corresponding neighboring pixels.

5. The apparatus of claim 4 wherein the gradient is an extended gradient.

6. The apparatus of claim 4 wherein the control circuit is configured to generate the reconstructed image by, at least in part, calculating a function of both the gradient as corresponds to the first image-representation channel for a given pixel and the gradient as corresponds to the second image-representation channel for the same given pixel.

7. The apparatus of claim 1 wherein the non-separable matrix-penalty of the Jacobian-matrix is a function of singular values of the Jacobian-matrix.

8. The apparatus of claim 7 wherein the function of the singular values of the Jacobian-matrix is a nuclear norm.

9. The apparatus of claim 1 further comprising:
third image-capture data regarding the scene formed using a third image-capture modality that is different from the first image-capture modality and the second image-capture modality;
wherein the fidelity error measure further measures the inconsistency of the image as compared to the third image-capture data.

10. The apparatus of claim 1 further comprising:
establishing a third image-representation channel;
wherein measuring the inconsistency of the image further comprises measuring the inconsistency of the image as compares to third image-representation channel data; and wherein scoring the image based on a priori likelihood or desirability further comprises scoring an image that further comprises third image-representation channel data.

11. The apparatus of claim 1 wherein the first image-representation channel comprises a first material basis and the second image-representation channel comprises a second material basis.

12. The apparatus of claim 1 wherein the control circuit is further configured to:
establish a first material basis;
establish a second material basis;
wherein the first image-representation channel describes image data as relates to the first material basis and the second image-representation channel describes image data as relates to the second material basis.

13. The apparatus of claim 1 wherein the iterative process comprises an iterative statistical reconstruction process.

14. The apparatus of claim 13 wherein the iterative statistical image reconstruction process comprises a computed tomography reconstruction process.

15. The apparatus of claim 13 wherein the iterative statistical image reconstruction process comprises a radiography-image reconstruction process.

16. A method by which a control circuit reconstructs an image using high energy-based data regarding a scene, the method including an iterative image reconstruction process that comprises:
by the control circuit:
accessing first image-capture data regarding the scene formed using a first image-capture modality;
accessing second image-capture data regarding the scene formed using a second image-capture modality that is different from the first image-capture modality;
establishing a first image-representation channel;
establishing a second image-representation channel;
establishing a fidelity error measure that, for any image containing first image-representation channel data and second image-representation channel data, measures inconsistency of the image as compared to the first image-capture data and the second image-capture data;
establishing a prior-penalty term that, for any image containing first image-representation channel data and second image-representation channel data, scores the image based on a priori likelihood or desirability using, at least in part, for each of a plurality of pixels for that image that contains the first image-representation channel data and the second image-representation channel data, a non-separable matrix-penalty of a Jacobian-matrix of the image at that pixel;
using an iterative process to generate a reconstructed image for which the reconstructed image at least approximately minimizes a combination of the fidelity error measure and the prior-penalty term.

17. The method of claim 16 wherein the non-separable matrix-penalty of the Jacobian-matrix is a function of singular values of the Jacobian-matrix.

18. The method of claim 17 wherein the function of the singular values of the Jacobian-matrix is a nuclear norm.

19. The method of claim 16 wherein the first image-representation channel comprises a first material basis and the second image-representation channel comprises a second material basis.

20. The method of claim 16 further comprising assessing a gradient for at least some of the individual pixels as compared to their corresponding neighboring pixels.

21. The method of claim 20 further comprising calculating a function of both the gradient as corresponds to the first image-representation channel for a given pixel and the gradient as corresponds to the second image-representation channel for the same given pixel.

* * * * *